United States Patent [19]

Nakayama et al.

[11] 4,415,497
[45] Nov. 15, 1983

[54] PROCESS FOR PRODUCING AN ANTIBIOTIC

[75] Inventors: Masahito Nakayama, Higashi-Yamato; Shigeru Kimura, Tachikawa; Toshimi Mizoguchi, Higashi-Murayama; Sohei Tanabe, Higashi-Murayama; Toshihito Mori, Higashi-Murayama, all of Japan

[73] Assignee: Kowa Co., Ltd., Nagoya, Japan

[21] Appl. No.: 296,306

[22] Filed: Aug. 26, 1981

[30] Foreign Application Priority Data

Sep. 5, 1980 [JP] Japan ............................... 55-123087

[51] Int. Cl.$^3$ ............................................ C07D 487/04
[52] U.S. Cl. ............................ 260/245.2 T; 424/274; 435/119
[58] Field of Search ............................. 260/245.2 T

[56] References Cited
U.S. PATENT DOCUMENTS 4,211,707 7/1980 Ratcliffe ..................... 260/245.2 T Primary Examiner—Mary C. Lee
Attorney, Agent, or Firm—Oblon, Fisher, Spivak, McClelland & Maier

[57] ABSTRACT

An antibiotic KA-6643-A or a salt thereof having the formula:

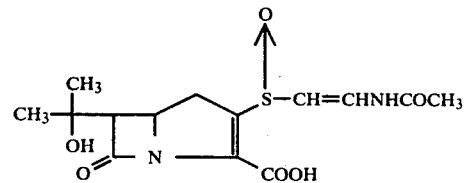

is produced by a process comprising the step of hydrolyzing an antibiotic KA-6643-B of the formula:

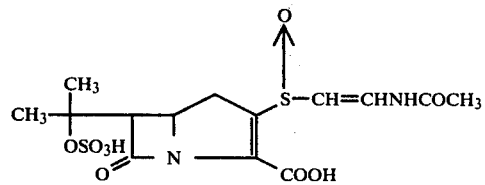

1 Claim, No Drawings

PROCESS FOR PRODUCING AN ANTIBIOTIC

BACKGROUND OF THE INVENTION

1. Field of the Invention

This invention relates to a novel process for producing an antibiotic KA-6643-A or a salt thereof.

2. Description of the Prior Art

The present inventors have found that a new strain KC-6643 belonging to the genus Streptomyces can prepare a novel antibiotic possessing potent antibacterial activity against gram-positive and gram-negative bacteria. As a result of this finding, they have succeeded in isolating antibiotics KA-6643-A and KA-6643-B as novel antibiotics from culture broths of such strain, as disclosed in co-pending United States patent application Ser. No. 137,259 in the names of the present inventors and other joint inventors.

In general, these novel antibiotics are represented by the formula (III):

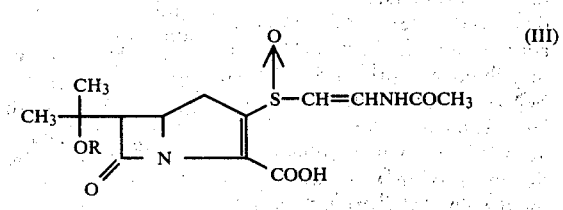

The formula (III) represents the KA-6643-A antibiotic when R is a hydrogen atom and the KA-6643-B antibiotic when R is a sulfonic acid group. Both the KA-6643-A antibiotic (hereinafter referred to as "KA-6643-A") and the KA-6643-B antibiotic (hereinafter referred to as "KA-6643-B") exhibit marked antibacterial potency. It has been found that the former is superior in the potency to the latter.

In various studies leading to the present invention, it has now been found that KA-6643-A can be easily obtained from conversion of KA-6643-B by hydrolysis.

SUMMARY OF THE INVENTION

Therefore, one object of the present invention is to provide a novel technique of producing KA-6643-A of excellent antibacterial characteristics with operationally and economically satisfactory results.

This object and other objects of the invention as hereinafter will become more readily apparent can be attained by a process for producing KA-6643-A or a salt thereof represented by the formula (I):

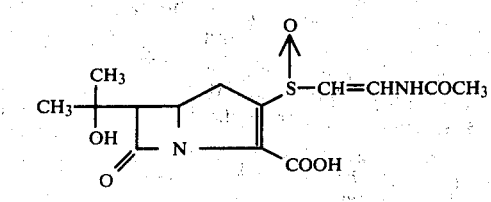

by hydrolyzing KA-6643-B represented by the formula (II):

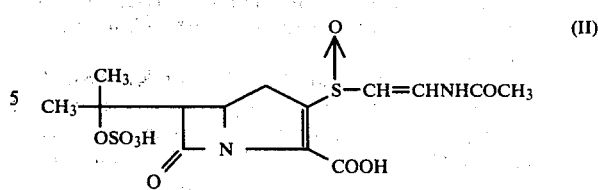

DESCRIPTION OF THE PREFERRED EMBODIMENTS

A KA-6643 substance exists in two isomeric forms, i.e., cis and trans forms because the substance contains a double bond in its side chain. The cis isomer is represented as the Z form and has the formula (IV):

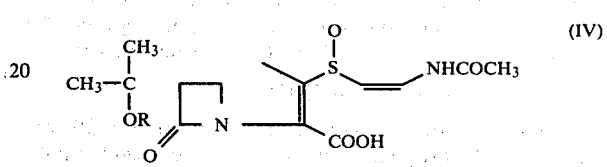

wherein R is a hydrogen atom or a sulfonic acid group, and the trans isomer is represented as the E form and has the formula (V):

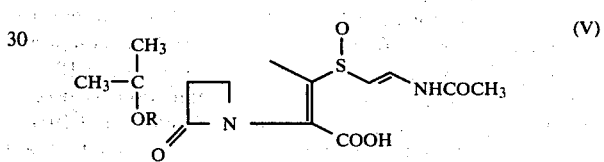

wherein R is the same as defined above.

As a metabolic product obtained is the E form. When reacted with a mercuric salt, however, the E form is convertible to the Z form, as taught in Japanese Patent Application No. 55-86989. Accordingly, it is possible to utilize either one of the E and Z forms as a raw material for the process of the present invention. Instead of isolating the KA-6643 substance either from a filtrate of a culture broth of a strain belonging to the genus Streptomyces and being capable of preparing the substance or from a crude active fraction obtained by culturing the strain, KA-6643-B may also be converted to KA-6643-A by hydrolyzing such culture broth filtrate or crude active fraction.

For the practice of the process according to this invention, the hydrolysis reaction is effected by acid hydrolysis, alkali hydrolysis or a similar type of reaction, or by contact with an ion-exchange resin.

Suitable acids for use in acid hydrolysis include inorganic acids such as phosphoric acid and sulfuric acid, and organic acids such as citric acid and oxalic acid. Suitable alkalis for use in alkali hydrolysis include sodium hydroxide, barium hydroxide and aqueous ammonia. Suitable ion-exchange resins include strong acid cation exchange resins such as Amberlite IRA-410, Amberlite IR-120 (Rohm and Haas Co.) and Dowex 50 (Dow Chemical Co.), and weak acid cation exchange resins such as Amberlite IRC-50, Amberlite IRC-84, Amberlite CG-50, Diaion WK-10 and Diaion WK-20 (Mitsubishi Chem. Ind., Ltd.).

An antioxidant such as acidic sodium sulfite, if desired, may be added to the hydrolysis reaction system.

The hydrolysis reaction is suitably carried out at temperatures of room temperature to 100° C. for periods of time for 1 to 10 hours.

The isolation of the desired product or KA-6643-A from the reaction mixture and subsequent purification of the product are achieved by any commonly used technique, preferably by gel filtration, column chromatography, reversed phase chromatography or freeze-drying, or any combination thereof.

If it becomes preferable, KA-6643-A may be converted to an alkali metal salt; an alkaline earth metal salt; a primary, secondary or tertiary amine salt; a quaternary ammonium salt; or a lower alkyl ester or fatty acid ester.

Having generally described the invention, a further understanding can be obtained by reference to Reference Example and certain specific Examples which are provided herein for purposes of illustration only and not intended to be limiting unless otherwise specified.

REFERENCE EXAMPLE (i) Into a medium which had a composition of 2% of starch, 1.5% of soybean flour, 0.28% of potassium phosphate monobasic, 0.18% of sodium phosphate dibasic.-dodecahydrate, 0.005% of cobalt chloride.hexahydrate, 0.05% of magnesium sulfate.heptahydrate and 0.001% of ferrous sulfate and which had been adjusted to a pH of 6.0 and sterilized were inoculated mycelia of a KC-6643 strain, followed by pre-culture at 27° C. for about 48 hours to give a first seed culture. Into each of two tanks each having a volume of 200 l was charged 100 l of another medium of the same composition as used above but having 1% of cotton seed oil added. The first seed culture was inoculated into each tank in an amount of 500 ml and cultured at 30° C. for 4 days by an aerated agitation system (rpm: 300, flow rate of air: 50 l/min).

(ii) After completion of the culture, 10 v/v % of Dicalite Perlite 4109 (Dicalite Orient Co., Ltd.) was added to the culture broth (170 l) as a filter aid, and the mycelia were removed by filtration. The resulting filtrate (150 l) was adjusted in its conductivity to 1.5 m /cm and passed through a column (21.5×45 cm) of a strong basic anion exchange resin, Diaion PA316 (Cl⁻type: Mitsubishi Chem. Ind., Ltd.) at a flow rate of 200 ml/min. After being washed with a 0.01M phosphate buffer solution (pH: 7.0), the resin was subjected to elution with a 0.01M phosphate buffer solution (pH: 7.0) containing 2M of sodium chloride in 2 v/v % of aqueous methanol at a flow rate of 150 ml/min to collent an active fraction. The resulting active fraction was passed through a column (16×10 cm) of Diaion HP-20, which had been adjusted with a 10 w/v % sodium chloride solution, at a flow rate of 400 ml/min and, after being washed with a 10 w/v % sodium chloride solution, was eluted with dionized water a flow rate of 200 ml/min to collect an active fraction.

(iii) The active fraction obtained in (ii) above was passed through a column (6×70 cm) of a strong basic anion exchange resin, Amberlite IRA-458 (Cl⁻type: Rohm & Haas Co.), at a flow rate of 50 ml/min and eluted with a 0.01M phosphate buffer solution (pH: 7.0) containing 0.15M sodium chloride to collect a fraction in which KA-6643-A was included. Thereafter, the fraction was eluted with a 0.01M phosphate buffer solution (pH: 7.0) containing 2M sodium chloride to yield an active fraction.

(iv) The active fraction obtained in (iii) above was passed through a column (6×70 cm) of Diaion HP-20 which had been pre-treated with a 20 w/v % aqueous sodium chloride solution, and eluted with deionized water at a flow rate of 20 ml/min to collect an active fraction. The active fraction was diluted with deionized water to have an electroconductivity of about 700 $\mu$ /cm and passed through a column (3×30 cm) of a weak basic anion exchange resin, DEAE-Sephadex A-25 (Pharmacia Fine Chemicals), which had been adjusted to a pH of 7.0 using a 0.01M phosphate buffer solution, followed by washing with water and by elution with a phosphate buffer solution (pH: 7.0) containing 0.15M of sodium chloride at a flow rate of 35 ml/min to collect an active fraction. The active fraction was concentrated under reduced pressure at below 30° C., passed through a column (3.5×40 cm) of Diaion HP-20 which had been pre-treated with a 10 w/v % aqueous sodium chloride solution, and then eluted with deionized water at a flow rate of 20 ml/min to collect an active fraction. The resulting active fraction was concentrated under reduced pressure to about 2 ml and freeze-dried to yield 190 mg of a crude powder of KA-6643-B. The thus obtained crude powder was dissolved in 1 ml of deionized water, passed through a column (2×30 cm) of Diaion HP-20 and thereafter eluted with deionized water at a flow rate of 1 ml/min to collect an active fraction. The active fraction was concentrated under reduced pressure and passed through a column of Sephadex G-10, followed by development with deionized water at a flow rate of 2.0 ml/min. The resulting active fraction was collected, concentrated under reduced pressure to about 2 ml and then freeze-dried to yield 80 mg of a crude powder.

(v) 80 mg of the crude powder obtained in (iv) above was dissolved in 0.1 ml of a 0.1M phosphate buffer solution (pH: 6.8) and passed through a column (0.8×120 cm) of Bondapack $C_{18}$/Polasil B (Waters Associates, Inc.) which had been pretreated with a 0.1M phosphate buffer solution, followed by elution with the same buffer solution at a flow rate of 6 ml/min to collect an active fraction. The active fraction was passed through a column (0.9×5 cm) of active carbon, washed with deionized water and then eluted with 50 w/v % aqueous acetone to collect an active fraction. The resulting active fraction was concentrated under reduced pressure to about 1 ml and freeze-dried to yield 35 mg of a pure powder of KA-6643-B.

EXAMPLE 1

80 mg of a sodium salt of KA-6643-B was dissolved in 2 ml of 0.1M phosphate buffer solution (pH: 7.0), and the solution was allowed to stand in a water bath at 70° C. for 4 hours. After being cooled to room temperature, the solution was passed through a column (8×1,200 mm) of Bondapak $C_{18}$ for adsorption. Elution was performed at a flow rate of 6 ml/min by use of a 0.05M phosphate buffer solution (pH: 6.8) containing 3% methanol. KA-6643-B was eluted after a retention time of 35 minutes, whereas KA-6643-A was eluted after a retention time of 120 minutes. The fraction containing KA-6643-A was collected and concentrated to about 5 ml under reduced pressure. The concentrate was passed through a column (20×200 mm) of Diaion HP-20 which had been pre-treated with a 10% sodium chloride solution and eluted with deionized water. The active fraction was collected and concentrated to about 2 ml. The concentrate was passed through a column (25×1,000 mm) of Sephadex G-10 and eluted with deionized water. The resulting active fraction was collected and freeze-dried to yield 2.2 mg of a sodium salt of KA-6643-A. The ultimate substance was identical with the authentic product derived from fermentation in terms of the physicochemical and biological properties.

EXAMPLE 2

60 mg of a sodium salt of KA-6643-B was dissolved in 10 ml of 0.1M acetate buffer solution (pH: 6.0), and the solution was allowed to stand in a water bath at 60° C. for 2.5 hours. After being cooled to room temperature, the solution was passed through a column (20×150 mm) of QAE-Sephadex A-25. Elution was performed by a concentration gradient method using a 0-0.9% sodium chloride solution. The active fraction was collected and concentrated to about 3 ml under reduced pressure. The concentrate was passed through a column (20×200 mm) of Diaion HP-20 pre-treated with a 10% sodium chloride solution and eluated with deionized water. The active fraction was collected and concentrated to about 2 ml under reduced pressure. The concentrate was passed through a column (25×1,000 mm) of Sephadex G-10 resulting and eluted with deionized water. The resulting active fraction was collected and freeze-dried to yield 1.8 mg of a sodium salt of KA-6643-A.

Having now fully described this invention, it will be apparent to one of ordinary skill in the art that many changes and modifications can be made to the invention without departing from the spirit or scope of the appended claims.

What is claimed as new and desired to be secured by Letters Patent is:

1. A process for producing an antibiotic KA-6643-A or a pharmaceutically acceptable salt thereof represented by the formula (I):

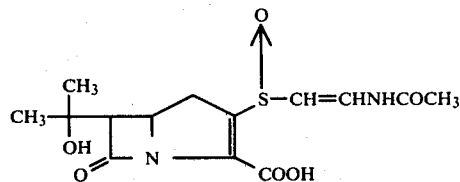

which comprises hydrolyzing an antibiotic KA-6643-B represented by the formula (II):

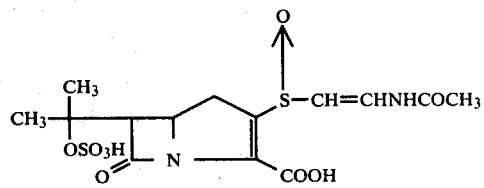

wherein said hydrolysis is carried out in an aqueous buffer solution at a pH in the range of from 6.0 to 7.0, at a temperature in the range of from room temperature to 100° C. and for a time of from 1 to 10 hours.

* * * * *